(12) United States Patent
Grablowitz et al.

(10) Patent No.: US 11,511,211 B2
(45) Date of Patent: Nov. 29, 2022

(54) DISTILLATIVE SEPARATION OF KETAZINE FROM POLYURETHANE DISPERSIONS

(71) Applicant: Covestro Deutschland AG, Leverkusen (DE)

(72) Inventors: Hans Georg Grablowitz, Cologne (DE); Alfred Zastrow, Dormagen (DE); Olaf Fleck, Bergisch-Gladbach (DE)

(73) Assignee: COVESTRO DEUTSCHLAND AG, Leverkusen (DE)

( * ) Notice: Subject to any disclaimer, the term of this patent is extended or adjusted under 35 U.S.C. 154(b) by 1006 days.

(21) Appl. No.: 16/311,010

(22) PCT Filed: Jun. 27, 2017

(86) PCT No.: PCT/EP2017/065880
§ 371 (c)(1),
(2) Date: Dec. 18, 2018

(87) PCT Pub. No.: WO2018/002067
PCT Pub. Date: Jan. 4, 2018

(65) Prior Publication Data
US 2020/0306660 A1    Oct. 1, 2020

(30) Foreign Application Priority Data
Jun. 28, 2016  (EP) .................................... 16176762

(51) Int. Cl.
| | |
|---|---|
| *B01D 3/10* | (2006.01) |
| *C08G 18/32* | (2006.01) |
| *C08G 18/10* | (2006.01) |
| *C08G 18/82* | (2006.01) |
| *C07C 243/16* | (2006.01) |
| *C08G 71/04* | (2006.01) |

(52) U.S. Cl.
CPC ............... *B01D 3/10* (2013.01); *C08G 18/10* (2013.01); *C08G 18/3231* (2013.01); *C08G 18/82* (2013.01); *C07C 243/16* (2013.01); *C08G 71/04* (2013.01)

(58) Field of Classification Search
CPC ....... C08G 18/10; C08G 18/3231; B01D 3/10
USPC ...................................... 528/68, 85
See application file for complete search history.

(56) References Cited

U.S. PATENT DOCUMENTS

2006/0241228 A1* 10/2006 Gertzmann ........ C08G 18/6625
                                                                524/376
2007/0167565 A1    7/2007  Rische et al.

FOREIGN PATENT DOCUMENTS

| CA | 1061043 A | 8/1979 |
|---|---|---|
| CA | 2253119 A1 | 5/1999 |
| DE | 2446440 A1 | 4/1976 |
| EP | 0916647 A2 | 5/1999 |

OTHER PUBLICATIONS

International Search Report for PCT/EP2017/065880 dated Aug. 25, 2017.
Written Opinion of the International Searching Authority for PCT/EP2017/065880 dated Aug. 25, 2017.

* cited by examiner

*Primary Examiner* — Michael J Feely
(74) *Attorney, Agent, or Firm* — Faegre Drinker Biddle & Reath LLP

(57) ABSTRACT

The present invention relates to a process for removing ketazine from polyurethane dispersions by means of distillation below the boiling point of ketazine.

9 Claims, No Drawings

DISTILLATIVE SEPARATION OF KETAZINE FROM POLYURETHANE DISPERSIONS

CROSS-REFERENCE TO RELATED APPLICATIONS

This application is a national stage application (under 35 U.S.C. § 371) of PCT/EP2017/065880, filed Jun. 27, 2017, which claims benefit of European Application No. 16176762.9, filed Jun. 28, 2016, both of which are incorporated herein by reference in their entirety.

The present invention relates to a process for removing ketazine from polyurethane dispersions by means of distillation below the boiling point of ketazine.

Aqueous polyurethane dispersions (PUDs) play an important role in coatings due to their particular properties. In addition to the technical advantages of polyurethanes, aqueous PU dispersions are advantageous since they contain only little or no organic solvent and thus make a contribution to durable and environmentally friendly coatings. PUDs are mainly produced by two different processes. In the so-called melt-dispersion process, firstly an isocyanate-functional hydrophilic prepolymer is prepared in the melt or frequently with the aid of a small proportion of a usually high-boiling solvent. In the next step, the prepolymer is dispersed in water and, to build up the molar mass, a chain extension is then usually carried out using polyamines or polyhydrazides in water. Since the solvent used commonly has a high boiling point, it cannot be subsequently removed and remains in the dispersion. In the so-called acetone process, initially an isocyanate-functional prepolymer is also prepared which is subsequently dissolved in acetone. The subsequent chain extension then takes place in the acetone solution of the prepolymer and the increase in the viscosity linked thereto may be controlled by the amount of acetone added. The dispersion is then effected in water and the acetone can be subsequently removed by distillation. Since in the acetone process no further and usually high-boiling solvent is used, the resulting dispersions are essentially free of organic solvents. The compounds for the chain extension are usually polyamines or polyhydrazides and hydrazine has proven its worth as standard compound, among others, since the dispersions reacted therewith have a significantly higher colour stability under thermal stress. If hydrazine is now added to such an acetone solution of prepolymer, it results in formation of a by-product where acetone and hydrazine react to give ketazine (or acetone azine) (cf. also E. C. Gilbert, Journal of the American Chemical Society, 51, 3394-3409, 1929). The ketazine formed remains in the dispersion due to its comparatively high boiling point (134° C. at standard pressure) and can, depending on the manufacturing process, hydrolyze again to the hydrazine, which is a major disadvantage due to the carcinogenic effect of hydrazine.

For this reason, there is a great demand for a process with which the ketazine formed as by-product can be removed from the dispersion with less effort and without impairment of the quality of the polyurethane dispersion. This object is achieved by the embodiments characterized in the patent claims and in the description of the present invention.

The temperature of the vapour phase is referred to as the vapour temperature and the temperature of the liquid phase is referred to as the bottom temperature.

In a first embodiment, the present invention relates to a process for removing ketazine from a polyurethane dispersion comprising the step of the distillation of the polyurethane dispersion, wherein the vapour temperature constantly exceeds the temperature at which removal of acetone is achieved by at maximum 10%.

The vapour temperature at which removal of acetone is achieved can be determined very simply by experiment. The bottom of the distillation plant is heated to the boiling point of acetone. The vapour temperature is initially below the bottom temperature since the low-boiling compounds are evaporated first. During the course of the distillation, the vapour temperature progressively increases since ever higher-boiling compounds are evaporated. By analyzing samples which are withdrawn on reaching defined vapour temperatures, the residual concentration of acetone present in the polyurethane dispersion at a given vapour temperature can be readily determined.

The term "removal of acetone" refers to a state of the polyurethane dispersion in which the acetone content is lower than 1% by weight.

It is additionally preferable that, in addition to the conditions mentioned above, the vapour temperature is at least around 15° C. below the boiling point of ketazine at the pressure prevailing in the distillation plant. The aforementioned temperature limit is preferably only briefly exceeded, particularly preferably not at all.

In the study on which the present invention is based, it has been found, surprisingly, that ketazine can be removed by distillation without increasing the temperature at the bottom of the distillation plant or in the vapour to the boiling point of ketazine. Since the acetone was completely removed on reaching a vapour temperature of 48° C. at the pressure of 120 mbar prevailing in the plant, whereas ketazine under these conditions has a boiling point of ca. 70° C., it was unexpected that already more than 90% of the ketazine originally present could be removed by continuing the distillation up to a vapour temperature of 51° C.

The term "removal of ketazine" refers to a state of the polyurethane dispersion in which the residual concentration of ketazine is preferably less than 1000 ppm, more preferably less than 500 ppm, even more preferably less than 300 ppm, even more preferably less than 200 ppm and most preferably less than 100 ppm. It is furthermore preferable that at least 90% of the ketazine originally present in the polyurethane dispersion is removed by the process according to the invention.

The dependence of the boiling point of a liquid on the ambient pressure is well known to those skilled in the art and therefore said person skilled in the art is easily capable of determining the temperature limits defined above for different pressures in the distillation plant. Table 1 lists the boiling points of ketazine at different pressures by way of example.

TABLE 1

| Pressure [mbar] | Boiling point of ketazine [° C.] |
| --- | --- |
| 1000 | 133 |
| 500 | 107 |
| 250 | 85 |
| 125 | 69 |

In a particularly preferred embodiment of the present invention, the distillation is carried out at a pressure of at most 140 mbar, particularly preferably at most 125 mbar. The distillation is carried out even more preferably at a pressure between 115 mbar and 125 mbar. In this case, a vapour temperature of 53° C. is not persistently exceeded. The distillation is carried out more preferably at a pressure between 115 mbar and 125 mbar.

A person skilled in the art knows that the pressure in the distillation plant does not have to be within the limits specified above during the entire distillation process. The distillation process can be commenced in accordance with the invention at atmospheric pressure, and then be continued at a continuously or stepwise reducing pressure. In this context, brief pressure rises are not harmful if they do not impair the distillation process.

In a preferred embodiment of the present invention, a bottom temperature of 53° C. is not persistently exceeded. The distillation is commenced preferably at a bottom temperature of 45° C.

In a preferred embodiment, the distillation is continued for at least two hours after reaching a temperature at the bottom of 48° C.

"Persistently" exceeding a temperature limit as understood in the present patent application signifies that, during the entire distillation process, the temperature limit specified is exceeded for at most 15 minutes, more preferably at most 10 minutes and most preferably at most 5 minutes. "Only briefly" exceeding a temperature limit signifies, in a mirror-like fashion, that the said temperature limit during the entire distillation process is exceeded for at most 15 minutes, more preferably at most 10 minutes and most preferably at most 5 minutes. The aforementioned periods refer to the entire period of exceeding the temperature, continuously or divided into at least two separate phases.

In a particularly preferred embodiment of the present invention, the distillation is continued, after reaching a vapour temperature at which removal of acetone is achieved, preferably for at least 120 minutes, more preferably for 30 minutes to 180 minutes, even more preferably for 60 minutes to 150 minutes, and most preferably for 90 minutes to 150 minutes.

The polyurethane dispersion from which the ketazine is removed by the process according to the invention, is preferably produced by the acetone process described in the introduction.

The polyurethane dispersions to be purified by the process according to the invention are produced from the prepolymers suitable for the production of polyurethane dispersions by chain extension.

The prepolymers suitable for the invention are typically the reaction products of one or more polyisocyanates with one or more compounds reactive to isocyanates, wherein the polyisocyanate or the polysocyanates is/are used in stoichiometric excess such that the prepolymer has terminal isocyanate groups.

The suitable prepolymers can be further differentiated into hydrophobic and hydrophilic prepolymers. The compounds referred to as hydrophobic prepolymers are those having no hydrophilic groups and therefore cannot be dissolved or dispersed in water. The compounds referred to as hydrophilic prepolymers are those compounds having covalently bonded hydrophilic groups which enable the prepolymer to be dissolved or to be dispersed in water.

Suitable polyisocyanates are aromatic, araliphatic, aliphatic or cydoaliphatic polyisocyanates. It is also possible to use mixtures of such polyisocyanates. Suitable polysocyanates are, for example, butylene diisocyanate, hexamethylene dilsocyanate (HDI), 1,5-pentamethylene dilsocyanate, isophorone diisocyanate (IPDI), 2,2,4- and/or 2,4,4-trimethylhexamethylene diisocyanate, the isomeric bis(4,4'-isocyanatocydohexyl)methanes or mixtures thereof in any isomeric content, isocyanatomethyl-1,8-octane dilsocyanate, 1,4-cydohexylene diisocyanate, 1,4-phenylene dilsocyanate, 2,4- and/or 2,6-tolylene dilsocyanate, 1,5-naphthylene-diisocyanate, 2,4'- or 4,4'-diphenylmethane dilsocyanate, triphenylmethane-4,4',4"-triisocyanate or derivatives thereof having urethane, isocyanurate, allophanate, bluret, uretdione or iminooxadiazinedione structure and mixtures of the same. Preference is given to hexamethylene dilsocyanate, isophorone dilsocyanate and the isomeric bis(4,4'-isocyanatocyclohexyl)methanes and also mixtures thereof.

The polyol reactive to isocyanate in the context of the present invention refers to a compound having 1-4, preferably 1.5-2.5 and especially preferably 1.9-2.1 groups reactive to isocyanate. Suitable groups reactive to isocyanate are groups known to those skilled in the art, such as hydroxyl groups, amine groups, hydrazide groups or thiol groups, preferably hydroxyl groups or amine groups, especially preferably hydroxyl groups.

The molar mass of suitable polyols is between 40 g/mol-13 000 g/mol and low molecular weight discrete compounds and/or higher molecular weight polydisperse compounds are suitable as polyols. The low molecular weight compounds are typically discrete compounds in the molar mass range between 40 and 499 g/mol. The higher molecular weight compounds are compounds having a molecular weight distribution and mean number-average molecular weights between 500 and 13 000, preferably between 700 g/mol and 4000 g/mol, especially preferably between 1000 g/mol and 3000 g/mol.

Suitable low molecular weight polyols are short-chain, i.e. comprising 2 to 20 carbon atoms, aliphatic, araliphatic or cycloaliphatic compounds. Examples of diols are ethylene glycol, diethylene glycol, triethylene glycol, tetraethylene glycol, dipropylene glycol, tripropylene glycol, 1,2-propanediol, 1,3-propanediol, 1,4-butanediol, neopentyl glycol, 2-ethyl-2-butylpropanediol, trimethylpentanediol, positionally isomeric diethyloctanediols, 1,3-butylene glycol, cydohexanediol, 1,4-cydohexanedimethanol, 1,6-hexanediol, 1,2- and 1,4-cydohexanediol, hydrogenated bisphenol A (2,2-bis(4-hydroxycyclohexyl)propane), 2,2-dimethyl-3-hydroxypropyl 2,2-dimethyl-3-hydroxypropionate. Preference is given to 1,4-butanediol, 1,4-cydohexanedimethanol and 1,6-hexanediol. Examples of suitable triols are trimethylolethane, trimethylolpropane or glycerol, preference being given to trimethylolpropane.

Examples of diamines are 1,2-ethylenediamine, 1,6-hexamethylenediamine, 1,4-butanediamine and isophoronediamine, particular preference being given to 1,2-ethylene diamine and isophoronediamine. Examples of dihydrazides are oxalic dihydrazide, carbohydrazide and adipic dihydrazide, particular preference being given to carbohydrazide and adipic dihydrazide. Examples of dithiols are 1,2-ethanedithiol, 1,3-propanedithiol, 1,4-butanedithiol and 1,6-hexanedithiol. Particular preference is given to 1,2-ethanedithiol and 1,6-hexanedithiol.

The low molecular weight compounds preferably used are diols.

The higher molecular weight compounds are in turn composed of monomers and, in addition to the usually terminal isocyanate-reactive end groups, have further functional groups along the main chain.

Suitable higher molecular weight polyols are polyester polyols, polyacrylate polyols, polyurethane polyols, polycarbonate polyols, polyether polyols, polyester polyacrylate polyols, polyurethane polyacrylate polyols, polyurethane polyester polyols, polyurethane polyether polyols, polyurethane polycarbonate polyols and polyester polycarbonate polyols, polyether polyamines and polyamidopolyamines, particular preference being given to polyester polyols, polyether polyols and polycarbonate polyols, particular preference being given to polyester polyols.

The suitable polyester polyols are commonly composed of one or more aliphatic and/or aromatic and/or araliphatic dicarboxylic acids with one or more aliphatic and/or aromatic and/or araliphatic diols incorporated and are produced via a polycondensation process.

Examples of polyester polyols that are of good suitability are the known polycondensates of di- and optionally tri- and tetraols and di- and optionally tri- and tetracarboxylic acids or hydroxycarboxylic acids or lactones. Instead of the free polycarboxylic acids, it is also possible to use the corresponding polycarboxylic anhydrides or corresponding polycarboxylic esters of lower alcohols to produce the polyesters. Examples of suitable diols are ethylene glycol, butylene glycol, diethylene glycol, triethylene glycol, polyalkylene glycols such as polyethylene glycol, and also propane-1,2-diol, propane-1,3-diol, butane-1,3-diol, butane-1,4-diol, hexane-1,6-diol and isomers, neopentyl glycol or hydroxypivalic acid neopentyl glycol ester, preference being given to the three latter compounds. In order to achieve a functionality <2, it is possible to use proportions of polyols having a functionality of 3, examples to be mentioned being trimethylolpropane, glycerol, erythritol, pentaerythritol, trimethylolbenzene or trishydroxyethyl isocyanurate.

Useful dicarboxylic acids include, for example, phthalic acid, isophthalic acid, terephthalic add, tetrahydrophthalic add, hexahydrophthalic add, cyclohexanedicarboxylic acid, adipic add, azelaic acid, sebacic add, glutaric add, tetrachlorophthalic acid, maleic add, fumaric add, taconic add, malonic add, suberic add, 2-methylsucdnic add, succinic acid, 3,3-diethylglutaric add, 2,2-dimethylsuccinic add. Anhydrides of these adds are likewise usable, where they exist. For the purposes of the present invention, the anhydrides are consequently covered by the expression "add". It is also possible to use monocarboxylic adds such as benzoic add and hexanecarboxylic add, provided that the mean functionality of the polyol is ≥2. Saturated aliphatic or aromatic adds are preferred, such as adipic add or isophthalic add. One example of a polycarboxylic add for optional additional use in smaller amounts is trimellitic acid.

Examples of hydroxycarboxylic adds that may be used as co-reactants in the production of a polyester polyol having terminal hydroxyl groups include hydroxycaproic add, hydroxybutyric add, hydroxydecanoic add, hydroxystearic add and the like. Usable lactones include ε-caprolactone, butyrolactone and homologues.

Preference is given to polyester polyols b) based on butanediol and/or neopentyl glycol and/or hexanediol and/or ethylene glycol and/or diethylene glycol with adipic acid and/or phthalic acid and/or isophthalic add. Particular preference is given to polyester polyols b) based on butanediol and/or neopentyl glycol and/or hexanediol with adipic acid and/or phthalic add.

Polyether polyols include, for example, the polyaddition products of the styrene oxides, of ethylene oxide, propylene oxide, tetrahydrofuran, butylene oxide, epichlorohydrin, and the mixed addition and grafting products thereof, and the polyether polyols obtained by condensation of polyhydric alcohols or mixtures thereof and those obtained by alkoxylation of polyhydric alcohols, amines and amino alcohols.

Suitable hydroxy-functional polyethers have OH functionalities of 1.5 to 6.0, preferably 1.8 to 3.0, OH numbers of 50 to 700 and preferably of 100 to 600 mg KOH/g of solids, and molecular weights Mn of 106 to 4000 g/mol, preferably of 200 to 3500, for example alkoxylation products of hydroxy-functional starter molecules such as ethylene glycol, propylene glycol, butanediol, hexanediol, trimethylolpropane, glycerol, pentaerythritol, sorbitol or mixtures of these and also other hydroxy-functional compounds with propylene oxide or butylene oxide. Preferred polyether components b) are polypropylene oxide polyols and polytetramethylene oxide polyols having a molecular weight of 300 to 4000 g/mol. In this context, the polyether polyols of particularly low molecular weight, given correspondingly high OH contents, may be water-soluble. Particular preference is given however to water-insoluble polypropylene oxide polyols and polytetramethylene oxide polyols having a molecular weight of 500-3000 g/mol and mixtures thereof.

The useful polycarbonate polyols are obtainable by reaction of carbonic add derivatives, for example diphenyl carbonate, dimethyl carbonate or phosgene, with diols. Useful diols of this kind include, for example, ethylene glycol, propane-1,2- and 1,3-diol, butane-1,3- and 1,4-diol, hexane-1,6-diol, octane-1,8-diol, neopentyl glycol, 1,4-bis-hydroxymethylcydohexane, 2-methylpropane-1,3-diol, 2,2,4-trimethylpentane-1,3-diol, dipropylene glycol, polypropylene glycols, dibutylene glycol, polybutylene glycols, bisphenol A, tetrabromobisphenol A, but also lactone-modified diols. Preferably, the diol component contains 40% to 100% by weight of hexane-1,6-diol and/or hexanediol derivatives, preferably those having not only terminal OH groups but also ether or ester groups, for example products which are obtained by reaction of 1 mol of hexanediol with at least 1 mol, preferably 1 to 2 mol, of ε-caprolactone, or by etherification of hexanediol with itself to give di- or trihexylene glycol. It is also possible to use polyether polycarbonate polyols.

Preference is given to polycarbonate polyols b) based on dimethyl carbonate and hexanediol and/or butanediol and/or scaprolactone. Very particular preference is given to polycarbonate polyols based on dimethyl carbonate and hexanediol and/or ε-caprolactone.

The hydrophilic prepolymers comprise further ionic groups and/or non-ionic hydrophilic groups in order to ensure sufficient dispersion of the resulting polyurethane dispersion in water. In this case, the ionic groups may be either cationic or anionic in nature. Compounds that act as cationic, anionic or non-ionic dispersants are those which comprise, for example, sulphonium, ammonium, phosphonium, carboxylate, sulphonate or phosphonate groups or groups which can be converted by salt formation to the aforementioned groups (potentially ionic groups) or polyether groups, and can be incorporated into the macromolecules via isocyanate-reactive groups present. The neutralizing agents required for salt formation may be added to the salt-forming groups either in a stoichiometric ratio or in excess. To generate anionic groups, organic bases such as tertiary amines or inorganic bases such as alkali metal hydroxides or ammonia are added. In this case, preference is given to using tertiary amines such as triethylamine, triethanolamine or dimethylethanolamine. Preferred suitable isocyanate-reactive groups are hydroxyl and amine groups.

Suitable ionic or potentially ionic compounds are, e.g. mono- and dihydroxycarboxylic add, dihydroxydicarboxylic add, mono- and diaminocarboxylic adds, mono- and dihydroxysulphonic acids, mono- and diaminosulphonic acids and also mono- and dihydroxyphosphonic adds or mono- and diaminophosphonic adds and salts thereof such as dimethylolpropionic add, dimethylolbutyric add, hydroxypivalic add, N-(2-aminoethyl)alanine, 2-(2-aminoethylamino)ethanesulphonic acid, ethylenediaminepropyl- or butyisulphonic add, 1,2- or 1,3-propylenediamineethylsulphonic add, malic acid, citric acid, glycolic acid, lactic acid, glycine, alanine, taurine, lysine, 3,5-diaminobenzoic add, an addition product of IPDI and acrylic acid (EP-A 0 916 647, Example 1) and the alkali metal and/or ammonium salts thereof; the adduct of sodium bisulphite onto but-2-ene-1, 4-diol, polyether sulphonate, the propoxylated adduct of 2-butenediol and NaHSO3, described, for example, In DE-A 2 446 440 (pages 5-9, formulae I-III) and units that can be converted to cationic groups, such as N-methyldiethanolamine, as hydrophilic formation components. Preferred ionic or potentially ionic compounds are those having carboxyl or carboxylate and/or sulphonate groups and/or ammonium groups.

Preferred compounds are polyether sulphonate, dimethylolpropionic acid, tartaric acid and dimethylolbutyric acid, particular preference being given to polyether sulphonate and dimethylolpropionic acid.

Suitable non-ionic hydrophilizing compounds are, for example, polyoxyalkylene ethers containing at least one hydroxyl or amino group. These polyethers contain a proportion of 30% by weight to 100% by weight of units derived from ethylene oxide. Useful compounds include polyethers of linear construction having a functionality between 1 and 3, but also compounds of the general formula (I),

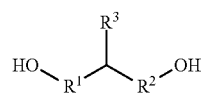

in which

R1 and R2 are each independently a divalent aliphatic, cydoaliphatic or aromatic radical which has 1 to 18 carbon atoms and may be interrupted by oxygen and/or nitrogen atoms, and R3 is an alkoxy-terminated polyethylene oxide radical.

Nonionic hydrophilizing compounds are, for example, also monovalent polyalkylene oxide polyether alcohols having a statistical average of 5 to 70, preferably 7 to 55, ethylene oxide units per molecule, as obtainable in a manner known per se by alkoxylation of suitable starter molecules (for example in Ullmanns Encydopädie der technischen Chemie, 4th edition, volume 19, Verlag Chemie, Weinheim pp. 31-38).

Examples of suitable starter molecules are saturated monoalcohols such as methanol, ethanol, n-propanol, iso-propanol, n-butanol, isobutanol, sec-butanol, the isomeric pentanols, hexanols, octanols and nonanols, n-decanol, n-dodecanol, n-tetradecanol, n-hexadecanol, n-octadecanol, cydohexanol, the isomeric methylcydohexanols or hydroxymethylcydohexane, 3-ethyl-3-hydroxymethyloxetane or tetrahydrofurfuryl alcohol, diethylene glycol monoalkyl ethers, for example diethylene glycol monobutyl ether, unsaturated alcohols such as allyl alcohol, 1,1-dimethylallyl alcohol or olein alcohol, aromatic alcohols such as phenol, the isomeric cresols or methoxyphenols, araliphatic alcohols such as benzyl alcohol, anisyl alcohol or cinnamyl alcohol, secondary monoamines such as dimethylamine, diethylamine, dipropylamine, diisopropylamine, dibutylamine, bis(2-ethylhexyl)amine, N-methyl- and N-ethylcyclohexylamine or dicyclohexylamine, and heterocyclic secondary amines such as morpholine, pyrrolidine, piperidine or 1H-pyrazole. Preferred starter molecules are saturated monoalcohols. Particular preference is given to using diethylene glycol monobutyl ether as starter molecule.

Alkylene oxides suitable for the alkoxylation reaction are especially ethylene oxide and propylene oxide, which can be used in the alkoxylation reaction in any sequence or else in a mixture.

The polyalkylene oxide polyether alcohols are either pure polyethylene oxide polyethers or mixed polyalkylene oxide polyethers, wherein the alkylene oxide units consist to an extent of at least 30 mol %, preferably to an extent of at least 40 mol %, of ethylene oxide units. Preferred non-ionic compounds are monofunctional mixed polyalkylene oxide polyethers having at least 40 mol % of ethylene oxide units and not more than 60 mol % of propylene oxide units.

Particular preference is given to monohydroxy-functional alkoxypolyethylene glycols such as MPEG 750 (Dow Chemical) and LB 25 (Bayer) and dihydroxy-functional compounds having lateral polyethylene oxide units such as Ymer N 120 (Perstorp) or Tegomer D 3404.

The molar ratio of NCO groups to isocyanate-reactive groups may vary here from 1.05-4.00, preferably from 1.2-3.0, particularly preferably from 1.4-2.5. The prepolymer is prepared by initially charging the appropriate polyol or a mixture of different polyols in a reaction vessel and subsequently adding the polyisocyanate or the mixture of polyisocyanates at elevated temperature. If mixtures of polyols and/or polyisocyanates are used, the individual reaction partners may then also be added at different time points in order to achieve a specific formation of the prepolymer. In this case, the reaction may be carried out either in the melt or in suitable inert solvents such as acetone or butanone. The reaction temperature here is between 50° C. and 130'C and the reaction time is 1 h-24 h. The urethanization reaction may be accelerated by using suitable catalysts. Suitable for this purpose are the catalysts known to those skilled in the art such as triethylamine, 1,4-diaz-abicyclo-[2,2,2]-octane, tin dioctoate, dibutyltin dilaurate or bismuth dioctoate, which are initially charged or metered in at a later stage. Preference is given to dibutyltin dilaurate. The reaction is then typically terminated when the NCO content no longer changes, the reaction typically being checked in this case by titration. In order to ensure the further processing of the prepolymers, low-viscosity prepolymers are generally advantageous, in addition to which, if not done during the preparation, the prepolymer is dissolved in a suitable solvent. Low-viscosity prepolymers or prepolymer solutions refers to those systems of which the viscosity is <104 mPas at a shear rate of 40 s−1. The prepolymer solution in this case preferably has a solids content of >40% and acetone is preferably used as solvent.

For the process according to the invention, preferred suitable polyurethane dispersions are those in which the chain extension is effected by hydrazine since ketazine may form as by-product in this case.

The examples which follow serve only to illustrate the invention. They are not intended to limit the scope of protection of the patent claims in any manner.

EXAMPLE 1: PREPARATION OF A CRUDE DISPERSION

The crude dispersion was prepared as follows: a polyester polyol and further polyols having a molar mass <400 g/mol were initially charged in a polymerization reactor and heated to 70° C. A polyisocyanate mixture was then metered in and the internal reactor temperature Increased to 100'C. The reaction mixture was stirred at 100'C until the theoretical NCO value of 4.47% by weight had been reached. The resulting isocyanate-functional prepolymer was then cooled to 60° C. and dissolved in acetone. After complete dissolution in acetone, the prepolymer solution was transferred to the distillation reactor and, at 40'C, the aqueous solution of a mixture of the sodium salt of aminoethylaminoethanesulphonic acid with hydrazine for the chain extension was added with stirring and the mixture then stirred for a further 15 min. Finally, the dispersion with water was carried out. The slightly milky polyurethane crude dispersion had a pH of 6.9 and a solids content of 23.8% by weight.

EXAMPLE 2 (COMPARATIVE): CONVENTIONAL DISTILLATION OF THE CRUDE DISPERSION

The crude dispersion was heated to 40° C. in the distillation reactor. A vacuum was then applied which was lowered stepwise to 120 mbar. After reaching 120 mbar, the bottom temperature and also the vapour temperature increased continuously. On reaching a vapour temperature of 48.5° C., the acetone content of the dispersion was below 1% by weight and the distillation was terminated.

The ketazine content at the end of the distillation was 1100 ppm.

EXAMPLE 3: INVENTIVE DISTILLATION PROCESS

The crude dispersion was heated to 40° C. in the distillation reactor. A vacuum was then applied which was lowered stepwise to 120 mbar. After reaching 120 mbar, the bottom temperature and also the vapour temperature increased continuously.

After reaching a vapour temperature of 48.5° C., the bottom temperature was increased to 51° C. over a time period of two hours at an unchanged pressure of 120 mbar.

At the end of the distillation process according to the invention, the ketazine content was 65 ppm.

The invention claimed is:

1. Process for the removal of acetone and a ketazine from an aqueous polyurethane dispersion comprising:
   providing an aqueous polyurethane dispersion containing acetone and a ketazine, wherein the ketazine is a reaction product of acetone and hydrazine;
   removing the acetone by distillation of the aqueous polyurethane dispersion at a selected pressure and an increasing vapour temperature until reaching a vapour temperature at which removal of the acetone is achieved; and
   continuing distillation at the selected pressure and an increased vapour temperature until removal of the ketazine is achieved; wherein the increased vapour temperature constantly exceeds the vapour temperature at which removal of the acetone is achieved by no more than 10%.

2. Process according to claim 1, wherein the selected pressure is at least 120 mbar and the increased vapour temperature is at most 53° C.

3. Process according to claim 2, wherein a bottom temperature during the continuing distillation is at most 53° C.

4. Process according to claim 2, wherein the removing of acetone by distillation is commenced with a bottom temperature of at most 45° C. and the continuing distillation is performed with an increased bottom temperature of up to a maximum of 53° C.

5. Process according to claim 2, wherein the selected pressure does not exceed 140 mbar.

6. Process according to claim 1, wherein the vapour temperature at which removal of the acetone is achieved is 48° C., and the continuing distillation takes place for at least two hours.

7. Process according to claim 1, wherein more than 90% of the ketazine originally present in the aqueous polyurethane dispersion is removed.

8. Process according to claim 1, wherein the polyurethane of the aqueous polyurethane dispersion was constructed by chain extension of an isocyanate-functional prepolymer with hydrazine.

9. Process according to claim 1, wherein the ketazine content of the aqueous polyurethane dispersion at the end of the continuing distillation is below 1000 ppm.

* * * * *